United States Patent
Young et al.

(10) Patent No.: US 7,744,596 B2
(45) Date of Patent: Jun. 29, 2010

(54) MAGNETICALLY AUGMENTED RADIO FREQUENCY ABLATION

(75) Inventors: Kimbolt Young, Newtonville, MA (US); Steven M. Anderson, Worcester, MA (US); John Spiridigliozzi, Brookline, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 819 days.

(21) Appl. No.: 11/250,063

(22) Filed: Oct. 13, 2005

(65) Prior Publication Data

US 2007/0088347 A1    Apr. 19, 2007

(51) Int. Cl.
*A61B 18/18* (2006.01)
(52) U.S. Cl. .............................. 606/41; 606/33; 606/40
(58) Field of Classification Search .................. 606/27, 606/33, 37, 40, 41, 49, 50; 430/270.1
See application file for complete search history.

(56) References Cited

U.S. PATENT DOCUMENTS

| | | | | |
|---|---|---|---|---|
| 3,489,095 A | * | 1/1970 | Eheim ......................... | 417/420 |
| 3,794,041 A | * | 2/1974 | Frei et al. .................... | 606/108 |
| 3,897,684 A | * | 8/1975 | Dewan ..................... | 73/861.13 |
| 4,162,672 A | * | 7/1979 | Yazaki ......................... | 600/15 |
| 4,271,782 A | * | 6/1981 | Bate et al. ................... | 118/623 |
| 5,429,131 A | * | 7/1995 | Scheinman et al. ......... | 600/374 |
| 5,628,771 A | * | 5/1997 | Mizukawa et al. .......... | 607/102 |
| 5,911,720 A | * | 6/1999 | Bourne et al. ................. | 606/41 |
| 6,006,756 A | * | 12/1999 | Shadduck .................... | 128/899 |

(Continued)

FOREIGN PATENT DOCUMENTS

EP          407057 A1 *   1/1991

(Continued)

OTHER PUBLICATIONS

PCT International Preliminary Report on Patentability of the International Bureau of PCT/US2006/039486, Applicant: Boston Scientific Scimed, Inc., Form PCT/IB/326, dated Apr. 24, 2008 (9 pages).

(Continued)

*Primary Examiner*—Linda C Dvorak
*Assistant Examiner*—Amanda Scott
(74) *Attorney, Agent, or Firm*—Vista IP Law Group LLP

(57) ABSTRACT

A tissue ablation assembly comprises an elongate probe device, at least one ablation electrode element carried by the probe device for conveying ablation energy, and at least one magnetic element for substantially altering the path of the ablation energy conveyed by the electrode element(s). In one embodiment, the magnetic element substantially urges the ablation energy radially outward. In another embodiment, magnetic element takes the form of a ring magnet that exhibits at least four alternating magnetic poles circumferentially disposed around the probe device axis. A method of treating tissue (e.g., a tumor) is also provided. The method comprises introducing a probe device into the patient, conveying ablation energy from the probe device, and applying a magnetic field adjacent the probe device to substantially alter the path of the ablation energy, e.g., by urging the ablation energy conveyed from the probe device radially outward into the tissue to create a tissue lesion, or by urging the ablation energy longitudinally.

13 Claims, 12 Drawing Sheets

U.S. PATENT DOCUMENTS

| | | | |
|---|---|---|---|
| 6,190,386 B1* | 2/2001 | Rydell | 606/51 |
| 6,292,678 B1* | 9/2001 | Hall et al. | 600/374 |
| 6,296,604 B1* | 10/2001 | Garibaldi et al. | 600/12 |
| 6,337,215 B1* | 1/2002 | Wilson | 436/526 |
| 6,379,353 B1* | 4/2002 | Nichols | 606/41 |
| 6,385,472 B1* | 5/2002 | Hall et al. | 600/374 |
| 6,432,136 B1* | 8/2002 | Weiss et al. | 623/3.1 |
| 6,533,777 B2* | 3/2003 | Won | 606/27 |
| 6,662,034 B2* | 12/2003 | Segner et al. | 600/373 |
| 6,689,128 B2* | 2/2004 | Sliwa et al. | 606/41 |
| 6,699,240 B2* | 3/2004 | Francischelli | 606/32 |
| 6,723,091 B2* | 4/2004 | Goble et al. | 606/41 |
| 6,961,620 B2* | 11/2005 | Rioux et al. | 607/99 |
| 6,971,391 B1* | 12/2005 | Wang et al. | 128/846 |
| 6,979,524 B2* | 12/2005 | Wago et al. | 430/270.1 |
| 7,207,989 B2* | 4/2007 | Pike et al. | 606/41 |
| 7,250,051 B2* | 7/2007 | Francischelli | 606/51 |
| 7,300,436 B2* | 11/2007 | Penny et al. | 606/34 |
| 2002/0022864 A1* | 2/2002 | Mahvi et al. | 607/2 |
| 2002/0042610 A1* | 4/2002 | Sliwa et al. | 606/27 |
| 2003/0073991 A1* | 4/2003 | Francischelli | 606/41 |
| 2004/0127895 A1* | 7/2004 | Flock et al. | 606/41 |
| 2004/0143260 A1* | 7/2004 | Francischelli | 606/41 |
| 2004/0147920 A1* | 7/2004 | Keidar | 606/34 |
| 2004/0231683 A1* | 11/2004 | Eng et al. | 128/899 |
| 2004/0260278 A1* | 12/2004 | Anderson et al. | 606/32 |
| 2004/0267106 A1* | 12/2004 | Segner et al. | 600/374 |
| 2005/0059852 A1 | 3/2005 | Rioux et al. | |
| 2005/0149012 A1* | 7/2005 | Penny et al. | 606/41 |
| 2005/0187545 A1* | 8/2005 | Hooven et al. | 606/41 |
| 2005/0203501 A1* | 9/2005 | Aldrich et al. | 606/27 |
| 2006/0009759 A1* | 1/2006 | Chrisitian et al. | 606/41 |
| 2006/0036236 A1* | 2/2006 | Rothstein et al. | 606/41 |
| 2006/0100620 A1* | 5/2006 | Daniel et al. | 606/49 |
| 2006/0142749 A1* | 6/2006 | Ivkov | 606/27 |
| 2006/0142757 A1* | 6/2006 | Daniel et al. | 606/50 |
| 2006/0195082 A1* | 8/2006 | Francischelli | 606/41 |
| 2006/0217707 A1* | 9/2006 | Daniel et al. | 606/50 |
| 2007/0088347 A1* | 4/2007 | Young et al. | 606/41 |
| 2007/0255276 A1* | 11/2007 | Sliwa et al. | 606/41 |
| 2007/0276363 A1* | 11/2007 | Patton et al. | 606/51 |
| 2008/0086140 A1* | 4/2008 | Wolf | 606/79 |
| 2008/0091193 A1* | 4/2008 | Kauphusman et al. | 606/41 |
| 2008/0161803 A1* | 7/2008 | Oral et al. | 606/41 |
| 2008/0161890 A1* | 7/2008 | Lafontaine | 607/105 |
| 2008/0167649 A1* | 7/2008 | Edwards et al. | 606/41 |
| 2008/0214988 A1* | 9/2008 | Altshuler et al. | 604/21 |
| 2008/0221650 A1* | 9/2008 | Turner et al. | 607/102 |

FOREIGN PATENT DOCUMENTS

| | | |
|---|---|---|
| WO | WO 96/29946 | 10/1996 |

OTHER PUBLICATIONS

PCT International Search Report for PCT/US2006/039486, Applicant: Boston Scientific Scimed, Inc., Form PCT/ISA/210 and 220, dated Apr. 13, 2006 (6 pages).

PCT Written Opinion of the International Search Authority for PCT/US2006/039486, Applicant: Boston Scientific Scimed, Inc., Form PCT/ISA/237, dated Apr. 13, 2006 (7 pages).

* cited by examiner

MAGNETICALLY AUGMENTED RADIO FREQUENCY ABLATION

FIELD OF THE INVENTION

The field of the invention relates generally to the structure and use of radio frequency (RF) electrosurgical probes for the treatment of tissue.

BACKGROUND

The delivery of radio frequency (RF) energy to target regions within tissue is known for a variety of purposes of particular interest to the present inventions. In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, non-insulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. PCT application WO 96/29946 and U.S. Pat. No. 6,379,353 disclose such probes. In U.S. Pat. No. 6,379,353, a probe system comprises a cannula having a needle electrode array reciprocatably mounted therein. The individual electrodes within the array have spring memory, so that they assume a radially outward, arcuate configuration as they are advanced distally from the cannula. In general, a multiple electrode array creates a larger lesion than that created by a single needle electrode.

In theory, RF ablation can be used to sculpt precisely the volume of necrosis to match the extent of the tumor. By varying the power output and the type of electrical waveform, it is possible to control the extent of heating, and thus, the resulting ablation. However, the size of tissue coagulation created from a single electrode, and to a lesser extent a multiple electrode array, has been limited by heat dispersion. As a consequence, when ablating lesions that are larger than the capability of the above-mentioned devices, the common practice is to stack ablations (i.e., perform multiple ablations) within a given area. This requires multiple electrode placements and ablations facilitated by the use of ultrasound imaging to visualize the electrode in relation to the target tissue. Because of the echogenic cloud created by the ablated tissue, however, this process often becomes difficult to accurately perform. This process considerably increases treatment duration and patent discomfort and requires significant skill for meticulous precision of probe placement.

In response to this, the marketplace has attempted to create larger lesions with a single probe insertion. Increasing generator output, however, has been generally unsuccessful for increasing lesion diameter, because an increased wattage is associated with a local increase of temperature to more than 100° C., which induces tissue vaporization and charring. This then increases local tissue impedance, limiting RF deposition, and therefore heat diffusion and associated coagulation necrosis. In addition, patient tolerance appears to be at the maximum using currently available 200 W generators.

It has been shown that the introduction of conductive material, such as metal or saline, into targeted tissue increases the tissue conductivity, thereby creating a larger lesion size. However, the introduction of additional conductive material into the patient typically either requires additional needle or probe insertions or a larger probe profile, thereby increasing the invasiveness of the ablation procedure, resulting in increased patient discomfort and recovery time.

For this reason, it would be desirable to provide improved electrosurgical methods and systems for more efficiently ablating tumors in the liver and other body organs without substantially increasing the profile of the ablation probe.

SUMMARY OF THE INVENTION

In accordance with the present inventions, a tissue ablation assembly is provided. The tissue ablation assembly comprises an elongate probe device having an axis. By way of non-limiting example, the elongate probe device may comprise a single probe shaft or may comprises a cannula and a reciprocatably disposed probe shaft. In one embodiment, the probe device is configured for being percutaneously introduced into a patient, although the probe device may alternatively be configured to be introducing into the patient in other ways, such as intravascularly, through an open surgical incision, or even through a natural orifice.

The tissue ablation assembly further comprises at least one ablation electrode element carried by the probe device for conveying ablation energy. The tissue ablation assembly may optionally comprise the radio frequency (RF) generator that conveys the ablation energy to the electrode element(s). Each or any of the electrode element(s) can, e.g., be a ring, needle or a rod or an array of electrode tines. If the elongate probe device comprises a single probe shaft, the electrode element can be mounted on the probe shaft, e.g., by interference fitting discrete electrodes onto the probe shaft, coating the probe shaft with an electrically conductive material, or by forming the probe shaft from an electrically conductive material, insulating it, and then removing selection regions of the insulation to expose the underlying electrically conductive core.

The electrode element(s) may be functionally configured in any one of a number of ways. For example, the electrode element(s) may comprise two electrode elements configured for conveying ablation energy therebetween, i.e., the electrode element(s) are placed in a bipolar arrangement. Or, the tissue ablation assembly may further comprise an external ground pad configured for receiving the ablation energy conveyed from the electrode element(s), i.e., the electrode element(s) are placed in a monopolar arrangement.

In accordance with one aspect of the present inventions, the tissue ablation assembly further comprises at least one magnetic element for substantially urging the ablation energy conveyed by the electrode element(s) radially outward relative to the probe device axis. By way of non-limiting example, this feature facilitates an increase in the resulting tissue ablation lesion without the need for introducing additional electrically conductive elements, such as saline or metal, into the tissue. Thus, ablation is less invasive when the magnetic element(s) is carried by the probe device, e.g., by mounting discrete magnetic element(s) on the probe device. Alternatively, any of the magnetic element(s) can be structurally disassociated with the probe device. To ensure that the ablation energy is radially urged outward in a substantial manner, the magnetic element(s) preferably generate a magnetic field strength of at least 500 Oersteds, and more preferably, greater than 5000 Oersteds. The magnetic element(s) can take the form of any element configured for generating a substantial magnetic field, such as a permanent magnet or electromagnet.

In accordance with another separate aspect of the present inventions, the tissue ablation assembly further comprises at least one magnetic element for substantially altering the path of the ablation energy conveyed by the electrode element(s).

The path of the ablation energy may be substantially altered, e.g., by urging the ablation energy radially outward relative to the probe device axis as described above, or by urging the ablation energy longitudinally relative to the probe device axis. By way of non-limiting example, this feature facilitates control and location of the resulting tissue ablation lesion. The structure and strength of the magnetic element(s) may be the same as that described above.

In accordance with still another separate aspect of the present inventions, the tissue ablation assembly further comprises a ring magnet carried by the probe device. The ring magnet can function in the same manner as the magnetic element(s) described above, with the exception that the ring magnet exhibits at least four alternating magnetic poles circumferentially disposed around the probe device axis. In one embodiment, the ring magnet comprises only four magnetic poles that are equidistantly disposed around the probe device axis. Although the present inventions should not be so limited in their broadest aspects, it has been discovered that this magnet configuration provides the most effective means for urging ablation energy outward in a radial direction.

In accordance with the present inventions, a method of treating tissue (e.g., a tumor) within a patient is provided. The method comprises introducing a probe device into the patient. The probe device may be percutaneously introduced into the patient, although other means of introducing the probe device into the patient can be used, e.g., intravascularly, through an open surgical incision, or even through a natural orifice. The method further comprises conveying ablation energy from the probe device, e.g., in a bipolar or monopolar fashion.

In accordance with one aspect of the present inventions, the method further comprises applying a magnetic field adjacent the probe device to substantially urge the ablation energy conveyed from the probe device radially outward into the tissue to create a tissue lesion. By way of non-limiting example, this feature facilitates an increase in the resulting tissue ablation lesion without introducing additional electrically conductive elements, such as saline or metal, into the tissue. For example, the magnetic field can enhance the size of the tissue lesion by at least twenty-five percent, and in some cases, greater than fifty percent. To ensure that the ablation lesion is radially urged outward in a substantial manner, the magnetic field preferably has a strength of at least 500 Oersteds, and more preferably, greater than 5000 Oersteds. In one method, the magnetic field is generated by the probe device, but in other methods, the magnetic field may be generated from other structures.

In accordance with another separate aspect of the present inventions, the method further comprises applying a magnetic field adjacent the probe device to substantially alter the path of the ablation energy conveyed from the probe device into the tissue. The path of the ablation energy may be substantially altered, e.g., by urging the ablation energy radially outward relative to the probe device axis as described above, or by urging the ablation energy longitudinally relative to the probe device axis. By way of non-limiting example, this feature facilitates control and location of the resulting tissue ablation lesion.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE ILLUSTRATED EMBODIMENTS

Figure 1:
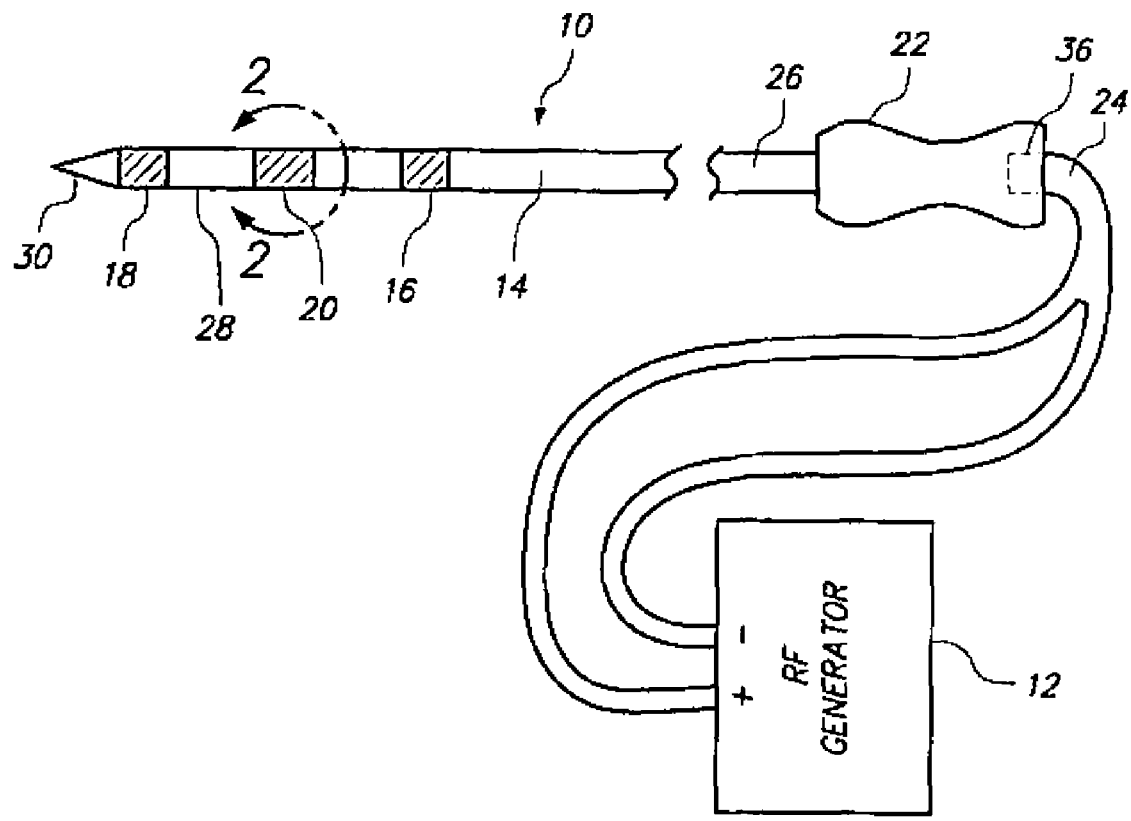
FIG. 1 is a plan view of a tissue ablation probe constructed in accordance with a preferred embodiment of the present invention.

FIG. 1 illustrates a tissue ablation probe 10 constructed in accordance with one embodiment of the present invention. The tissue ablation probe 10 generally comprises an elongated probe shaft 14 for introduction into a patient adjacent targeted tissue to be treated, a pair of bipolar ablation electrodes (a proximal electrode 16 and a distal electrode 18) disposed on the probe shaft 14 for conveying radio frequency (RF) ablation energy through the target tissue region, a magnetic element 20 mounted on the probe shaft 14 for magnetically augmenting the ablation energy, and a handle 22 mounted on the probe shaft 14 for facilitating handling of the tissue ablation probe 10 by the physician and for providing a means for connecting to a radio frequency (RF) generator 12 via RF cable 24.

The RF generator 12 may be a conventional RF power supply that operates at a frequency in the range from 200 KHz to 4 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

The probe shaft 14 has a proximal end 26 on which the handle 22 is mounted, and a distal end 28 on which the ablation electrodes 16, 18 and magnetic element 20 are disposed. In the illustrated embodiment, the probe shaft is rigid or semi-rigid and comprises a tissue penetrating distal tip 30 to facilitate the percutaneous introduction of the ablation probe 10 into the patient. In the illustrated embodiment, the probe shaft 14 comprises a metallic core 32 composed of a biocompatible material, such as stainless steel, and an electrically insulative layer 34 disposed over the metallic core 32 (best shown in FIG. 2). Alternatively, the probe shaft 14 may be composed of an electrically insulative material, such as a medical grade plastic, in which case, a separate insulative coating is not needed. The probe shaft 14 has a suitable length, typically in the range from 5 cm to 30 cm, preferably from 10 cm to 20 cm, an outside diameter consistent with its intended use, typically being from 1 mm to 5 mm, usually from 1.3 mm to 4 mm, and an inner diameter typically being from 0.7 mm to 4 mm, preferably from 1 mm to 3.5 mm.

The distal ablation electrode 18 is formed on the probe shaft 14 just proximal to the distal tip 30, and the proximal ablation electrode 16 is formed on the probe shaft 14 proximally from the distal ablation electrode 18. Although not illustrated, the distal tip 30 of the probe shaft 14 may help form the distal ablation electrode 18. To facilitate the bipolar nature of the ablation probe 10, the distance between the electrodes 16, 18 is preferably within the range of 0.5 cm-4 cm, more preferably within the range of 0.75 cm-2 cm. The ablation electrodes 16, 18 may be formed on the probe shaft 14 in any of a variety of manners that preserves the bipolar nature of the ablation probe 10.

For example, one of the electrodes 16, 18 can be formed by exposing the metallic shaft core 32 through the insulative layer 34, and the other of the electrodes 16, 18 can be formed by interference fitting a discrete ring electrode over the insulative layer 34, completing an electrical connection back to the generator through an insulated wire running along probe shaft 14. Alternatively, both electrodes 16, 18 can take the form of discrete ring electrodes that are interference fit over the insulative layer 34. If the core of the probe shaft 14 is alternatively composed of an electrically insulative material, both electrodes 16, 18 can be placed into direct contact with two conductors inside the core of the probe shaft 14, for example, by interference fitting discrete ring electrodes, or even by coating the external probe shaft 14 with an electrically conductive material in the electrode regions.

It is preferred that the outer diameter of the electrodes 16, 18 be flush with the outer diameter of the probe shaft 14, so that the probe shaft 14 can be smoothly introduced though tissue without hindrance from the electrodes 16, 18. To this end, in the case where the electrodes 16, 18 take the form of discrete electrode elements with finite thicknesses, the core of the probe shaft 14 (whether metallic or insulative) preferably comprises annular recesses (not shown) in which the electrodes 16, 18 will be disposed.

The handle 22 is preferably composed of a durable and rigid material, such as medical grade plastic, and is ergonomically molded to allow a physician to more easily manipulate the ablation probe 10. The handle 22 comprises an electrical connector 36 with which the RF cable 24 mates. In the illustrated embodiment, the electrical connector 36 is electrically coupled to the electrodes 16, 18 via separate insulative RF wires (not shown), which may be routed through the wall of the probe shaft 14 or a lumen (not shown) extending within the probe shaft 14. Alternatively, if one of the electrodes 16, 18 is in direct contact with the metallic shaft core 32, the electrical connector 36 can be electrically coupled to this electrode via the shaft core 32.

Figure 3:
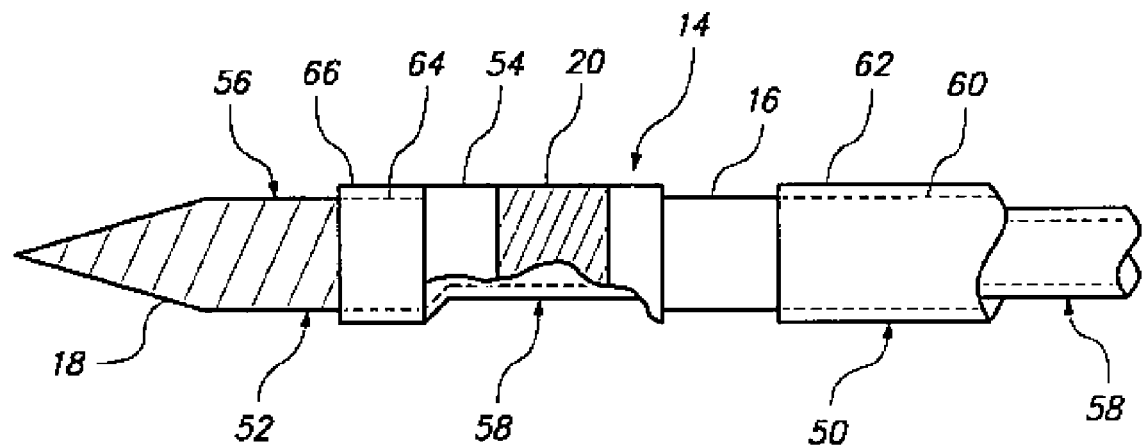
FIG. 3 is a partially cutaway view of an alternative embodiment of a probe shaft used in the ablation probe of FIG. 1.

In an alternative embodiment illustrated in FIG. 3, the probe shaft 14 is constructed in such a manner that eliminates the use of RF wires altogether. To this end, the probe shaft 14 comprises proximal and distal tubes 50 and 52, as well as a medial tube 54, that are fitted together to form an integrated probe shaft with bipolar ablation capability. The distal tube 52 has a distal portion 56 on which the distal ablation electrode 18 is disposed, and a tapered or necked-down portion 58 that proximally extends back to the handle 22. The proximal tube 50, which carries the proximal ablation electrode 16 and also proximally extends back to the handle 22, is fitted over the neck-down portion 58 of the distal tube 52. The medial tube 54 is fitted over the necked-down portion 58 of the distal tube 52 between the distal end of the proximal tube 50 and the proximal edge of the distal portion 56 of the distal tube 50. It should be appreciated that the thickness of the medial tube 54 compensates for the discontinuity created between the proximal and distal tubes 50, 52. To this end, the outer profiles of the proximal tube 50, distal portion 56 of the distal tube 50, and medial tube 54 are similar so that the outer profile of the completed probe shaft 14 is contiguous.

In the embodiment illustrated in FIG. 3, the proximal and distal tubes 50, 52 are configured in a manner that allows RF energy to be delivered to the electrodes 16, 18, while electrically isolating the electrodes 16, 18 from each other. In particular, the proximal tube 50 comprises an electrically conductive core 60, e.g., stainless steel (shown partially in phantom) and an electrically insulative coating 62 disposed over the conductive core 60. Likewise, the distal tube 52 comprises an electrically conductive core 64 (shown partially in phantom) and an electrically insulative coating 66 disposed over the conductive core 64. The proximal ends of the conductive cores 60, 64 are electrically coupled to the electrical connector 36 described above (not shown in FIG. 3) in a bipolar fashion. The respective electrodes 16, 18 are conveniently formed onto the proximal and distal tubes 50, 52 by removing portions of the insulative coatings 62, 66 to expose the underlying conductive material. The medial tube 54 is composed of an electrically insulative material to ensure that the electrodes 16, 18 are electrically isolated from each other. The magnetic element 20 is mounted around the medial tube 54, so that it is electrically insulated from the electrodes 16, 18.

Figure 4:
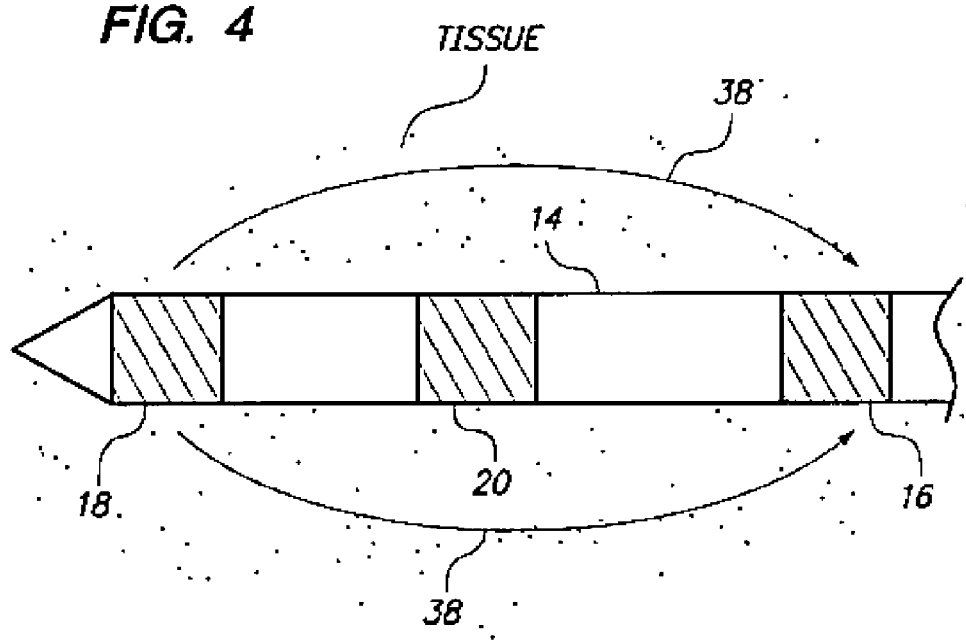
FIG. 4 is a partially cutaway plan view of the tissue ablation probe of FIG. 1, particularly illustrating the path that ablation energy is conveyed between bipolar electrodes of the tissue ablation probe.

Referring back to FIG. 1, the RF cable 24 leading from the electrical connector 36 is connected to the positive and negative poles (or vice versa) of the RF generator 12, such that RF energy is delivered from the RF generator to the ablation electrodes 16, 18 in a bipolar fashion. That is, as illustrated in FIG. 4, ablation energy will be conveyed from the positive pole of the RF generator 12 to one of the ablation electrodes 16, 18 (in this case, the distal electrode 18), follow a path 38 through the tissue from the distal electrode 18 to the other of the ablation electrodes 16, 18 (in this case, the proximal electrode 16), and then be conveyed from the proximal electrode 16 back to the negative pole of the RF generator 12.

Figure 5:
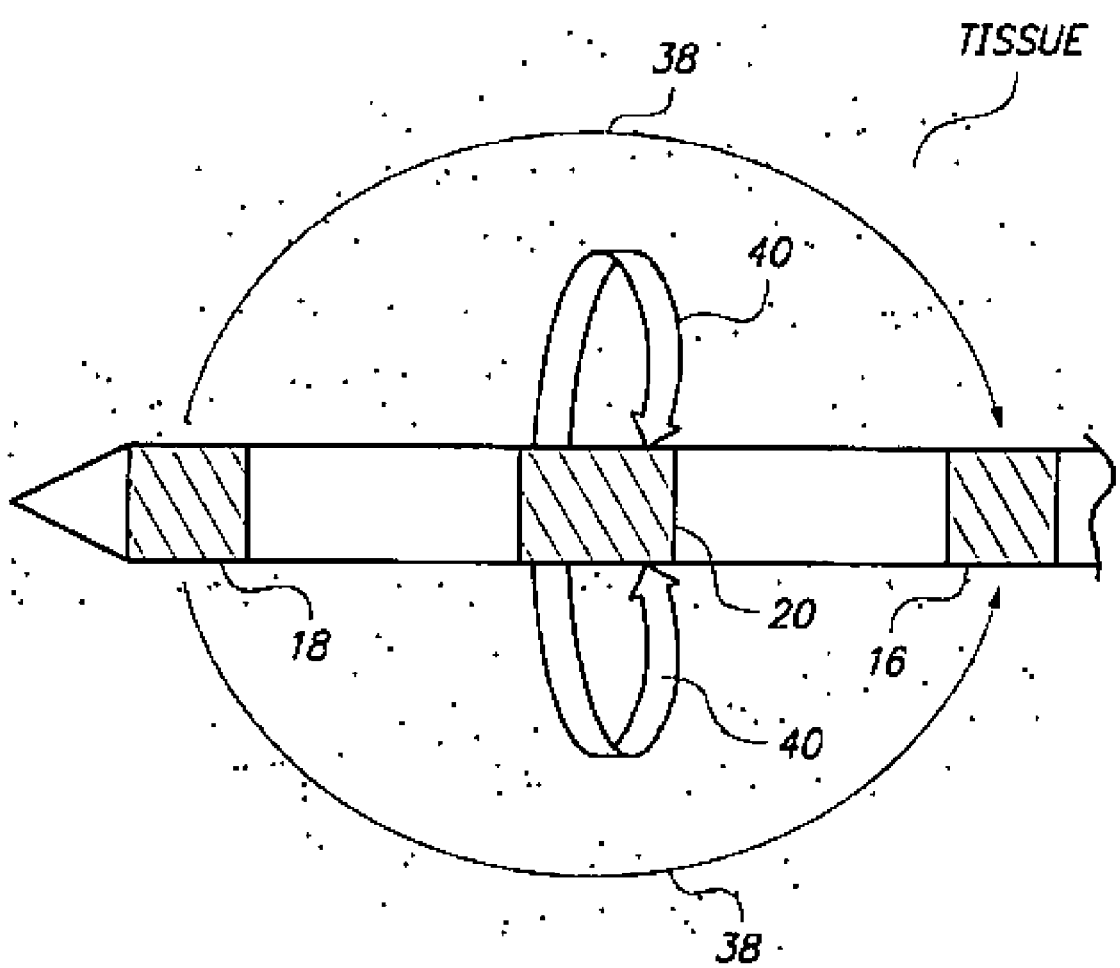
FIG. 5 is a partially cutaway plan view of the tissue ablation probe of FIG. 4, particularly illustrating the effect that the magnetic field generated by the magnetic element of FIG. 2 has on the ablation energy path.

As illustrated in FIG. 5, the magnetic element 20, which is axially centered between the ablation electrodes 16, 18, generates a magnetic field (represented by magnetic flux lines 40) that alters the path 38 of the ablation energy conveyed through the tissue. In this embodiment, the magnetic flux lines 40 generated by the magnetic element 20 urges the ablation energy radially outward relative to the axis of the probe shaft 14. In this manner, a greater volume of tissue is exposed to the ablation energy, thereby advantageously resulting in a larger lesion. It should be noted that the magnetic element 20 need not be centered exactly between the ablation electrodes 16, 18. However, the magnetic element 20 is preferably located somewhere between the ablation electrodes 16, 18 to maximize the effect that the generated magnetic field has on the path 38 of the ablation energy as it passes through the tissue between the ablation electrodes 16, 18.

It is noted that while all objects, including the probe shaft 14, will generate a magnetic field that alters the path of electrical energy—albeit at an extremely low and unnoticeable level, the magnetic element 20 generates a sizable magnetic field that substantially alters the path of the ablation energy. For the purposes of this specification, a magnetic field alters the path of ablation energy in a substantial manner if the tissue lesion resulting from the altered ablation energy is visually greater than the tissue lesion that would have otherwise resulted in the absence of the magnetic field. By way of non-limiting example, an alteration of the ablation energy path that results in an increase of a lesion volume of at least twenty-five percent falls well within the range considered to be substantial. In the preferred embodiment, to ensure that the ablation energy path is substantially altered, the magnetic element 20 generates a magnetic field having a flux strength that is at least 500 Oersteds, preferably at least 5000 Oersteds.

The magnetic element 20 can take the form of an element that generates a substantial magnetic field. For example, the magnetic element 20 can comprise a permanent magnetic material, such as cast or sintered almico, ceramic (hard ferrite), samarium cobalt, neodymium-iron-boron, etc. Alternatively, the magnetic element 20 can take the form of an electromagnet connected to wires (not shown) that are passed in conventional fashion through the probe shaft 14 to the electrical connector 36. In this case, an alternating current (AC) source for powering the magnetic element 20 may be either provided in the RF generator 12 or a separate unit.

Figure 2:
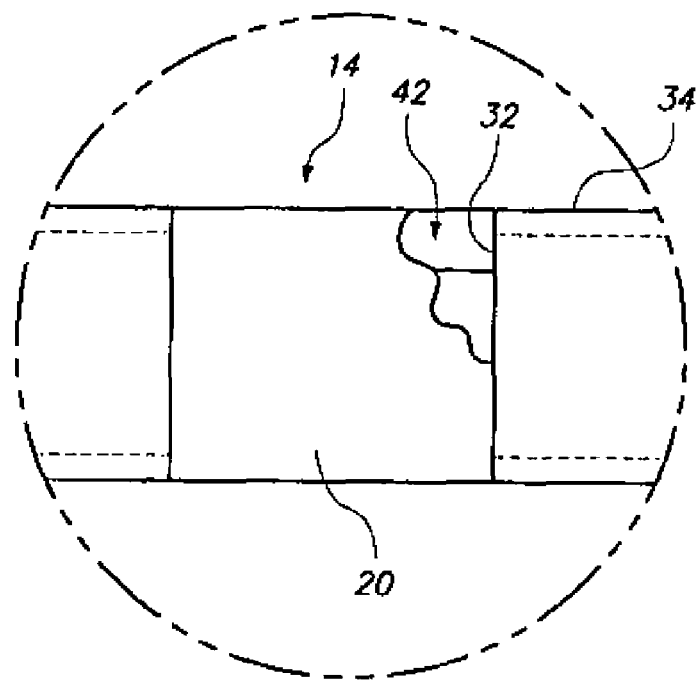
FIG. 2 is a magnified view of a magnetic element carried by the tissue ablation probe of FIG. 1.

In the embodiment illustrated in FIG. 1, the magnetic element 20 takes the form of a ring magnet that is suitably mounted to the probe shaft 14. As with the electrodes 16, 18, the probe shaft 14 preferably comprises an annular recess 42 in which the magnetic element 20 will be mounted, as illustrated in FIG. 2. If the magnetic element 20 is relatively thick, the annular recess 42 will be formed in the metallic probe core 32, so that the outer diameter of the magnetic element 20 remains flush with the outer diameter of the probe shaft 14. If the metallic shaft core 32 is used to convey ablation energy to one of the ablation electrodes 16, 18, the magnetic element 20 preferably does not directly contact the metallic core 32, so that the magnetic element 20 does not act as an electrode. In this case, an insulative material is preferably provided between the inner surface of the magnetic element 20 and the metallic shaft core 32, e.g., by extending the insulation layer 34 into the annular recess 42 or by coating the inner surface of the magnetic element 20 with an insulative material. In the alternative embodiment illustrated in FIG. 3, the annular recess (not shown) in which the magnetic element 20 is mounted is formed within the insulative tube 54.

Figure 6:
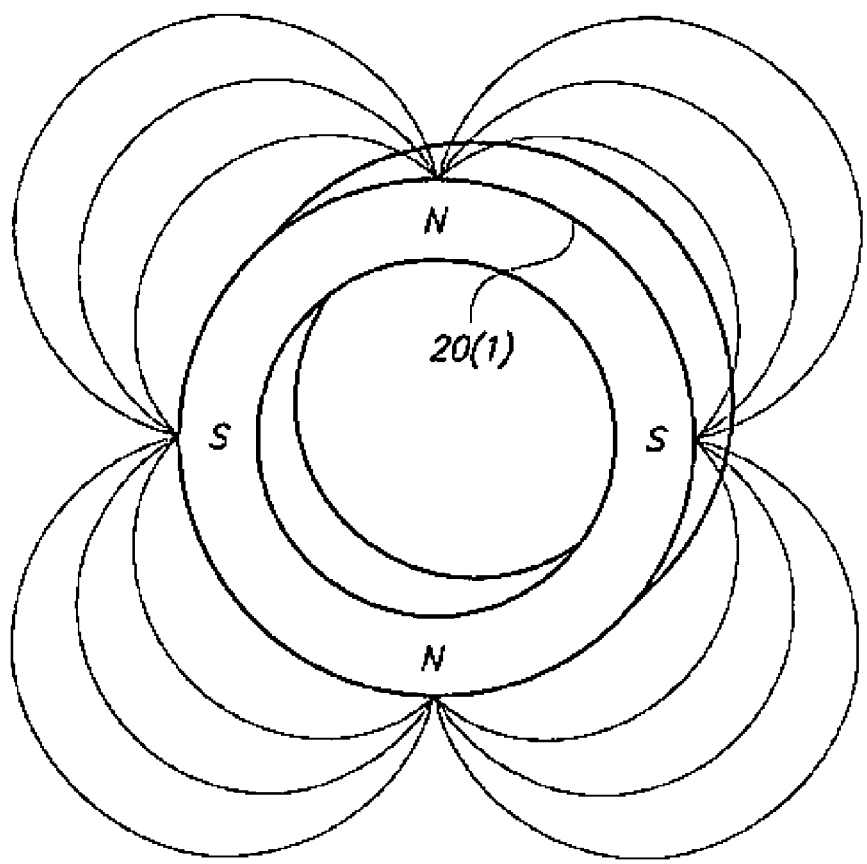
FIG. 6 is a perspective view of one embodiment of the magnetic element of FIG. 2.

It has been discovered that the use of a permanent four-pole ring magnet 20(1) as the magnetic element 20 is the most efficient and effective means of generating a magnetic field having a magnitude and flux line pattern sufficient to radially urge the ablation energy outward in a substantial manner. In particular, and with reference to FIG. 6, the ring magnet 20(1) has four alternating north and south magnetic poles circumferentially disposed about its axis. That is, the ring magnetic 20(1) has two North poles in the 12 and 6 o'clock positions, and two South poles in the 3 and 9 o'clock positions, such that a clover-leaf magnetic flux pattern is formed around the ring magnet 20(1) in the plane in which the ring magnet 20(1) lies. As can be appreciated, each lobe of the clover-leaf magnetic flux pattern will serve to push the ablation energy radially outward.

Figure 7:
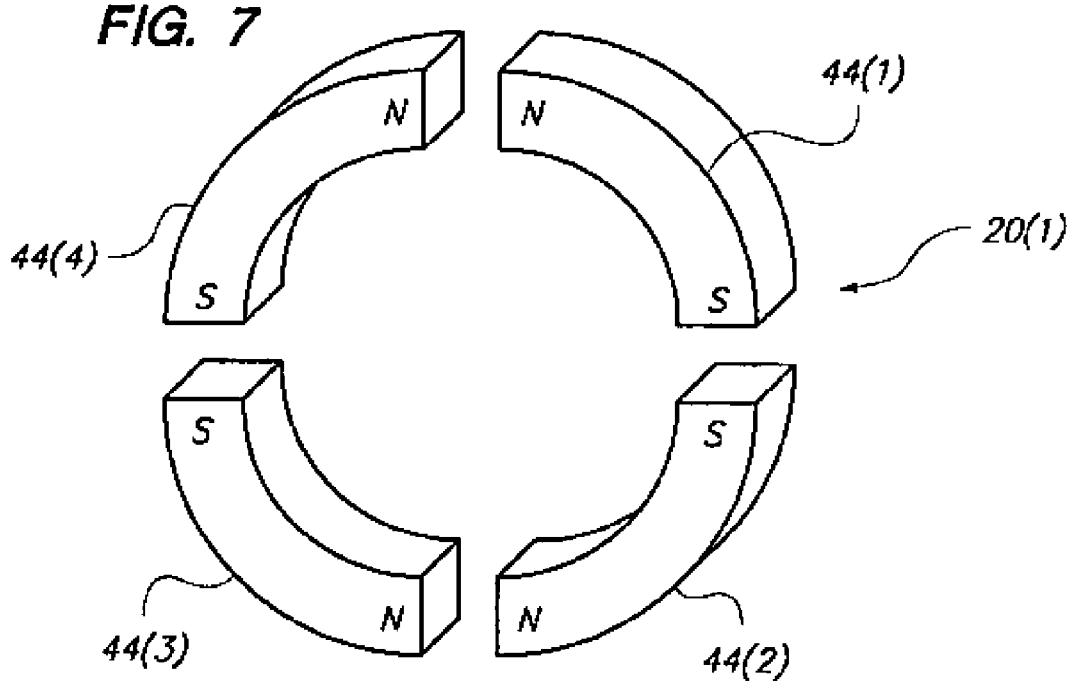
FIG. 7 is an exploded view of the magnetic element of FIG. 6.

The ring magnet 20(1) can be manufactured by bonding four arcuate magnetic sectors 44(1)-(4) together, as illustrated in FIG. 7. As can be seen, each magnetic sector 44 has North and South poles at its respective opposing ends. Magnetic polarities of the magnetic sectors 44(1) and 44(3) are opposite to the magnetic polarities of the magnetic sectors 44(2) and 44(4), so that the opposing poles of each magnetic sector 44 matches the poles of the two magnetic sectors 44 bonded to the respective magnetic sector 44. It has been demonstrated that the 4-pole ring magnet 20(1) illustrated in FIGS. 6 and 7 results in an increase in the lesion size of at least fifty percent.

Figure 8:
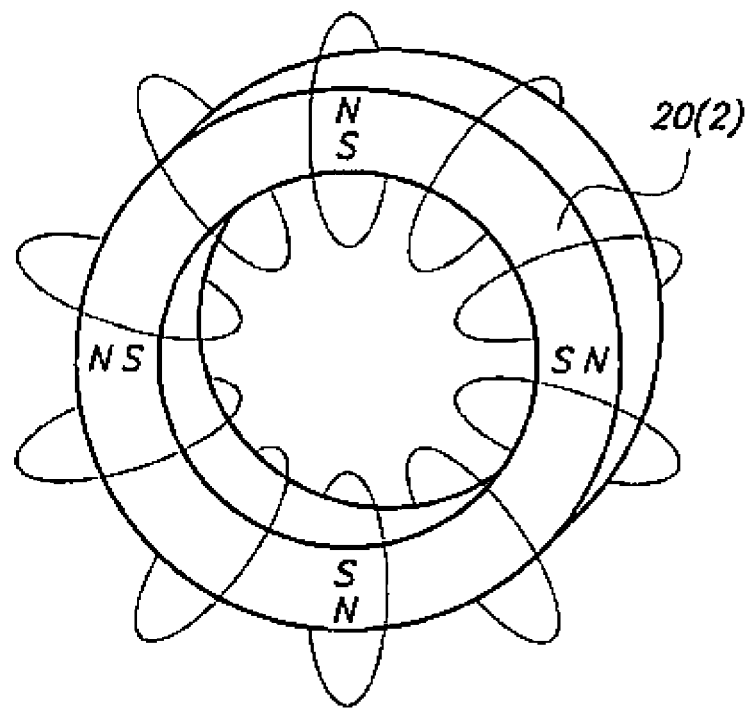
FIG. 8 is a perspective view of another embodiment of the magnetic element of FIG. 2, particularly illustrating the magnetic field generated thereby.

Referring to FIG. 8, an alternative ring magnet 20(2) is shown. In contrast to the four-pole ring magnet 20(1) illustrated in FIG. 5, the ring magnet 20(2) has two poles—i.e., a North pole on the inner circumferential portion of the ring magnet 20(2) and a South pole on the outer circumferential portion of the ring magnet 20(2). As a result, a magnetic flux pattern, which extends from the inner surface to the outer surface of the ring magnet 20(2) is generated.

Thus, like the ring magnet 20(1) described above, the magnetic field of the ring magnet 20(2) urges the ablation energy radially outward into the tissue. However, the strength of the magnetic field generated by the ring magnet 20(2) is somewhat limited in that the magnetic flux lines cannot extend past the center of ring magnet 20(2). In contrast, the magnetic flux lines of the ring magnet 20(1) illustrated in FIG. 6 may extend radially outward a distance equal to many multiples of the diameter of the ring magnet 20(1). This is significant, since the diameter of the ring magnet will be limited to the diameter of the probe shaft, which is preferably made as small as possible to minimize the invasiveness of the ablation probe 10. It is believed that the ring magnet 20(2) illustrated in FIG. 8 may be used in cases where maximization of the magnetic flux is not required or desired.

Having described the structure of the tissue ablation probe 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 $cm^3$ to 150 $cm^3$, and often from 2 $cm^3$ to 35 $cm^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 9A:
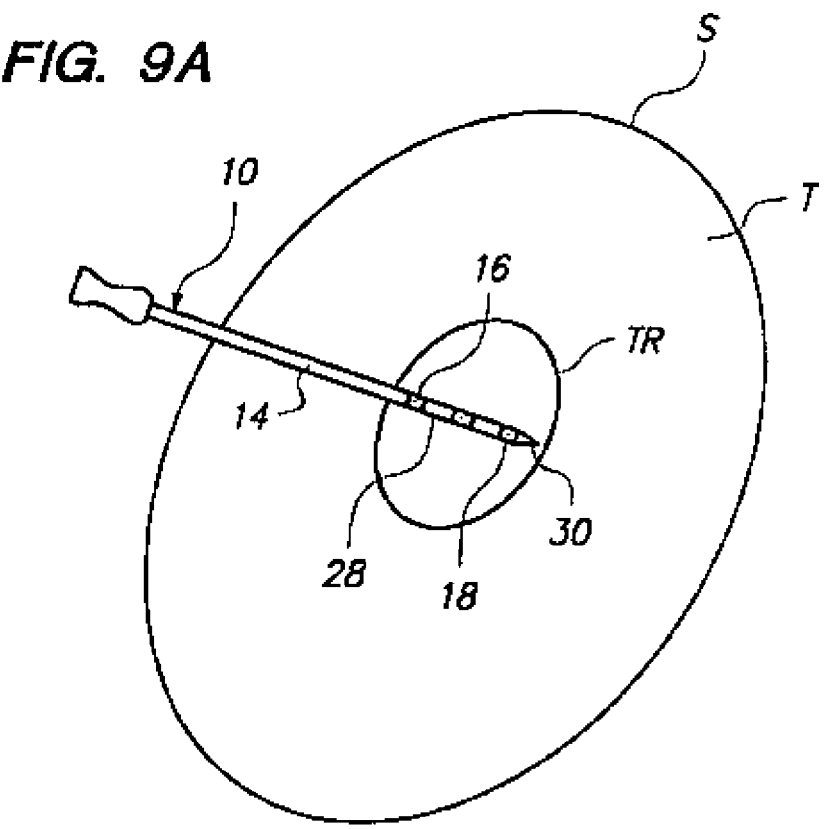
FIGS. 9A-9C are side views illustrating a method of ablating tissue using the tissue ablation probe of FIG. 1.
Figure 9B:
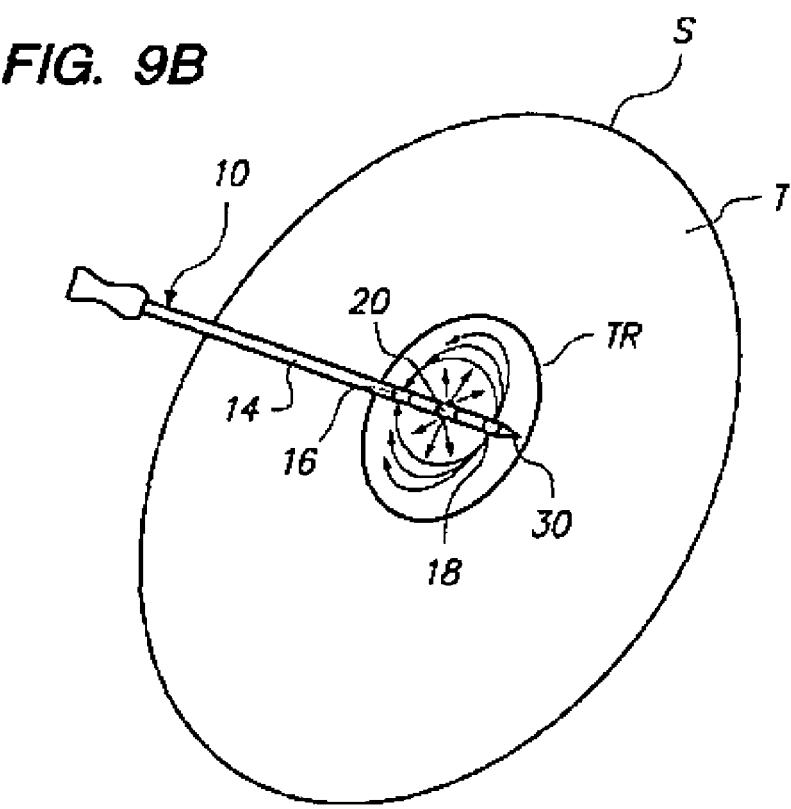
Figure 9C:
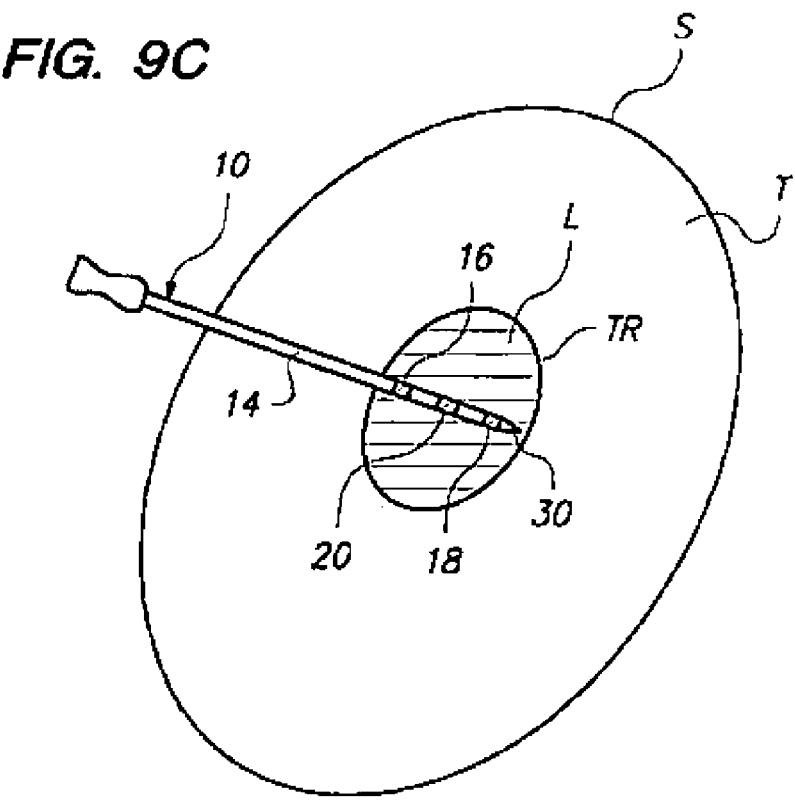

Referring now to FIGS. 9A-9C, the operation of the tissue ablation probe 10 is described in treating a treatment region TR within tissue T located beneath the skin or an organ surface S of a patient. The ablation probe 10 is first introduced through the tissue T, so that the ablation electrodes 16, 18 are located on opposite sides of the treatment region TR and generally equidistance from the center of the treatment region TR (FIG. 9A). This can be accomplished using any one of a variety of techniques. In the preferred method, the ablation probe 10 is introduced to the treatment region TR percutaneously directly through the patient's skin or through an open surgical incision. In this case, the sharpened tip 30 of the probe shaft 14 facilitates introduction to the treatment region TR. In such cases, it is desirable that the probe shaft 14 be sufficiently rigid, i.e., have a sufficient column strength, so that it can be accurately advanced through tissue T.

In other cases, the ablation probe 10 may be introduced using an internal stylet that is subsequently exchanged for the ablation probe 10. In this latter case, the probe shaft 14 can be relatively flexible, since the initial column strength will be provided by the stylet. More alternatively, a component or element may be provided for introducing the ablation probe 10 to the treatment region TR. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The ablation probe 10 can then be introduced through the sheath lumen, so that the distal end 28 of the probe shaft 14 advances from the sheath into the treatment region TR.

Once the electrodes 16, 18 are properly positioned, the RF generator 12 is then connected to the electrical connector 36 (shown in FIG. 1), and then operated to transmit RF ablation energy between the ablation electrodes 16, 18. That is, ablation energy 38 is conveyed from the distal ablation electrode 18 through the treatment region TR to the proximal ablation electrode 16 (FIG. 9B). At the same time, the magnetic element 20 generates the magnetic field 40 that urges the ablation energy radially outward further into the treatment region TR. As a result, an ablation lesion L, which will eventually expand to include the entire treatment region TR, is created (FIG. 9C).

It should be noted that because the performance of a permanent magnet deteriorates when exposed to heat over time, the ablation probe 10, if the magnetic element 20 is formed of a permanently magnetic material, will have a limited life. This may be advantageous if it is desired that the ablation probe 10 be limited to single-use. However, if it desired that the ablation probe 10 be used for multiple ablations during a single treatment, e.g., if the patient has several tumors, the deteriorated performance of the magnet element 20 may be disadvantageous in this respect. This disadvantage may be overcome by mounting the magnetic element 20 to the probe shaft 14 in a removable manner.

Figure 10:
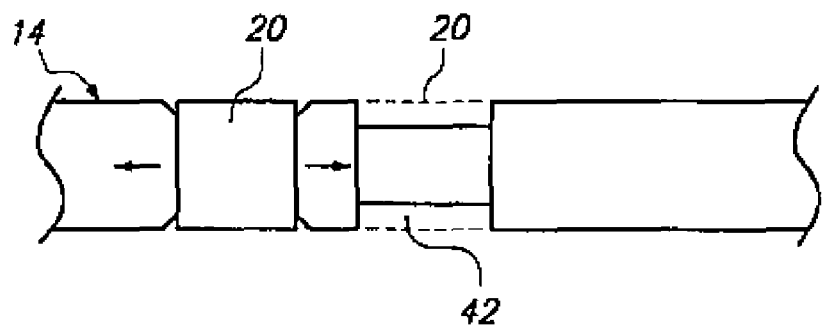
FIG. 10 is a partially cutaway plan view of the tissue ablation probe of FIG. 1, particularly showing the magnetic element of FIG. 2 as being removable.

For example, in the case where the magnetic element 20 takes the form of a ring magnet, its inner diameter may be smaller than the outer diameter of the insulated portion of the probe shaft 14, thereby allowing the ring magnet to be slipped over the probe shaft 14 in a tightly toleranced manner by virtue of the resiliency of the insulation layer 34, and into the annular recess 42 in a snap-fit arrangement (shown in phantom), and conversely removed from the annular recess 42 and slipped off of the probe shaft 14, as illustrated in FIG. 10.

To allow the thickness of the magnetic element 20 to be increased, while enabling its outer surface to still be flush with the outer surface of the probe shaft 14, the magnetic element 20 can be cut so that its inner diameter can be expanded to accommodate the insulative portion of the probe shaft 14—much like a clip ring. When the magnetic element 20 engages the annular recess 42, the resiliency of the magnetic element 20 will cause its inner diameter to decrease, so that it conforms to the probe shaft 14 in a fixed and stable manner. Alternatively, the magnetic element 20 can be composed of two separable halves (not shown, which can be placed on two opposing sides of the annular recess 42 and locked together, e.g., in a snap fit arrangement, to affix the magnetic element 20 onto the probe shaft 14.

Operation of this embodiment in ablating a treatment region will be similar to that described above with respect to FIGS. 9A-9C, with the exception that it can be used to create multiple lesions over an extended period of ablation time. In this case, the user will remove the used magnetic element 20 from the probe shaft 14 and install a new magnetic element 20 on the probe shaft (e.g., by slipping the magnetic element 20 over the distal end 28 of the probe shaft 14) between ablations.

Although the previous embodiments have been described as having a single ring magnet, other types and numbers of magnetic elements may be used. For example, referring to FIG. 11, an alternative embodiment of a tissue ablation probe 110 will now be described. The tissue ablation probe 110 is similar to the previously described ablation probe 10, with the exception that it comprises two magnetic elements, and in particular, a proximal cylindrical bar magnet 120 and a distal cylindrical bar magnet 121 (both shown in phantom), which are suitably mounted within the center of the probe shaft 14 adjacent each other. To force the magnetic flux lines 140 radially outward, the respective South poles of the magnets 120, 121 face each other.

Figure 11:
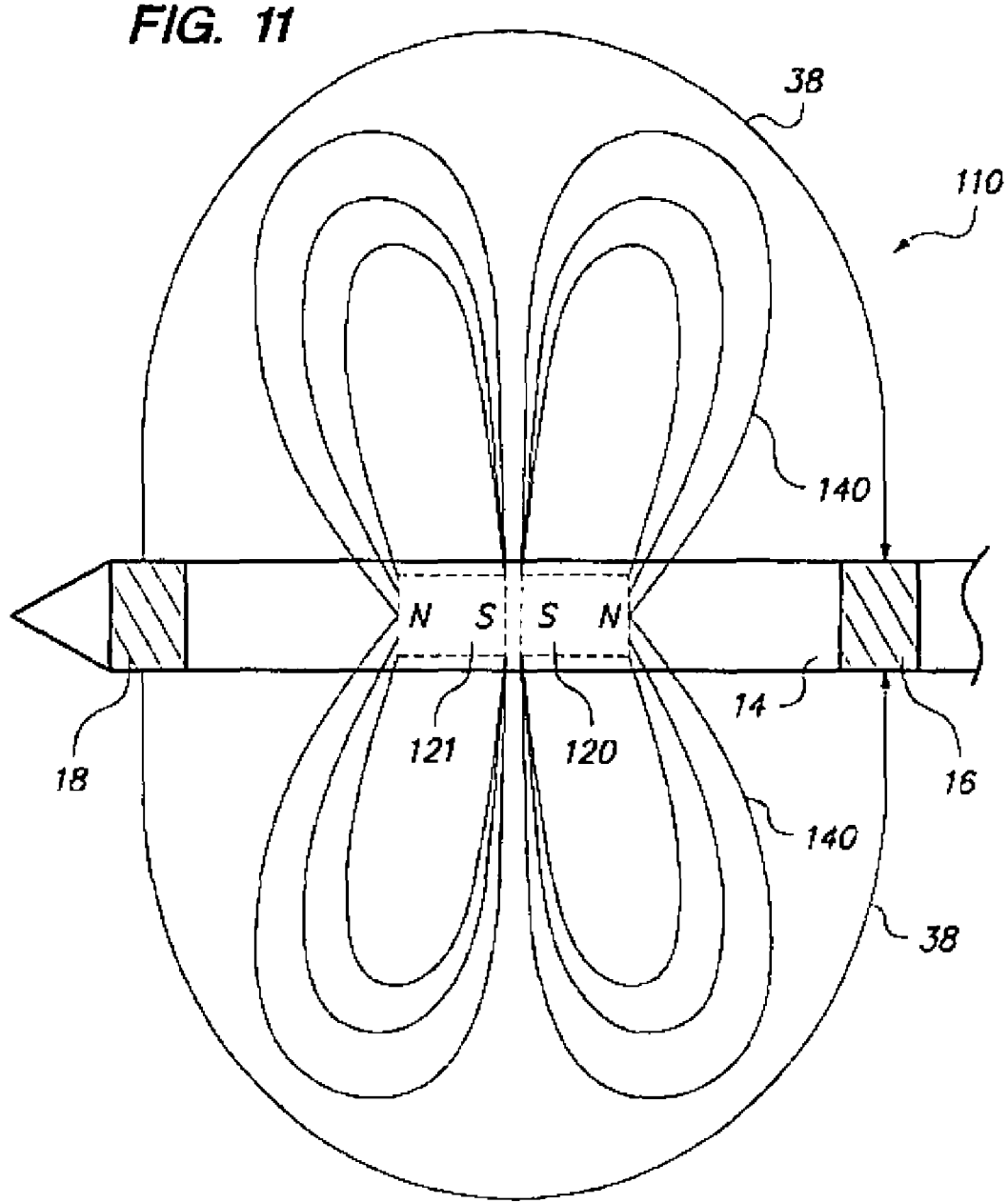
FIG. 11 is partially cutaway plan view of a tissue ablation probe constructed in accordance with another embodiment of the present invention.

As can be seen in FIG. 11, the magnetic flux lines 140 adjacent the respective South poles of the magnetic elements 120, 121 extend radially outward in a direction perpendicular to the axis of the probe shaft 14, so that the ablation energy 38 conveyed from the distal ablation electrode 18 to the proximal ablation electrode 16 is urged radially outward. In contrast, if a single bar magnet were used, or if the opposite poles of the magnetic elements 120, 121 were placed adjacent each other, the magnetic flux lines would have more of an oblong pattern that extends along the axis of the probe shaft 14. In this case, the radial presence of the resulting magnetic field would be greatly diminished, thereby limiting the radially expanding effect that it would have on the ablation energy. The tissue ablation probe 110 can be operated in the same manner described above with respect to FIGS. 9A-9C to ablate a treatment region.

Figure 12:
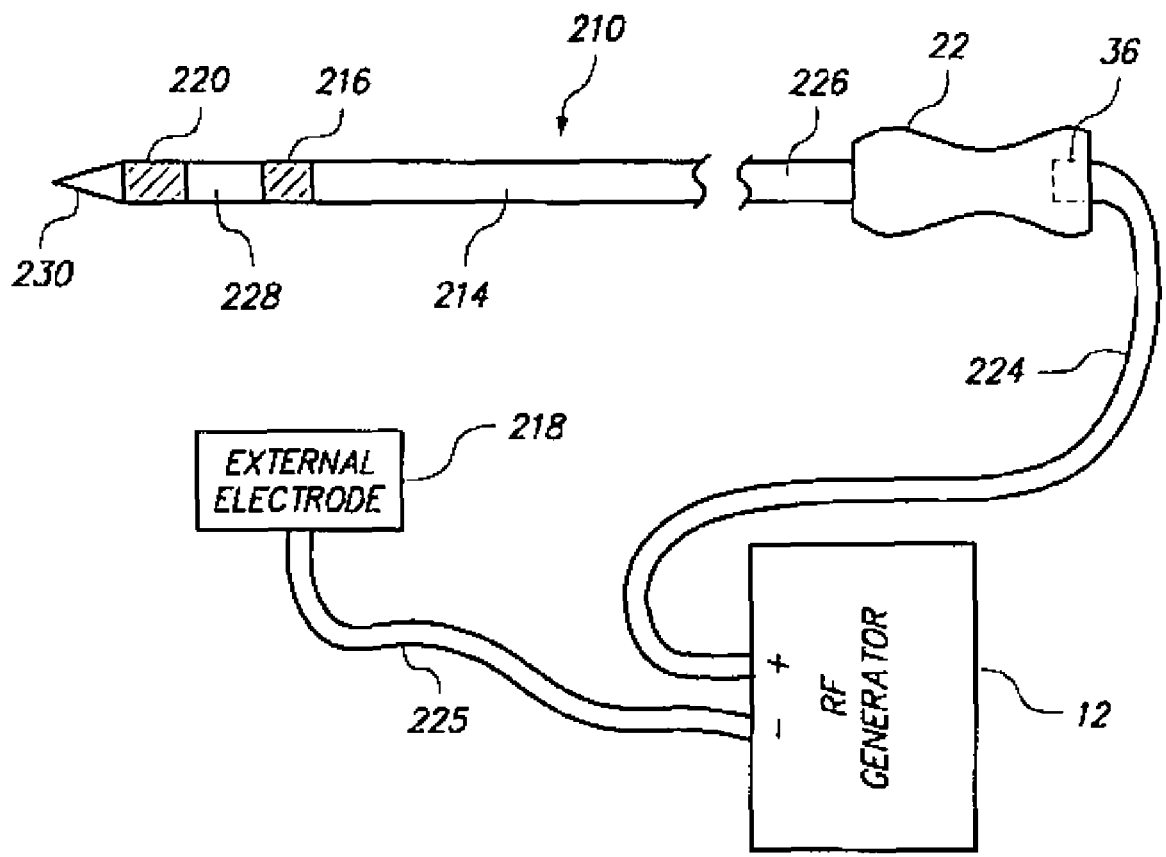
FIG. 12 is plan view of a tissue ablation probe constructed in accordance with still another embodiment of the present invention.

Although the tissue ablation probes 10, 110 have been described as bipolar tissue ablation probes, monopolar tissue ablation probes with magnetically augmented ablation energy can also be used. For example, FIG. 12 illustrates a monopolar tissue ablation probe 210. The ablation probe 210 is similar to the previously described ablation probe 10, with the exception that the ablation probe 210 has a single ablation electrode 216.

In particular, ablation probe 210 comprises a probe shaft 214 having a proximal end 226 on which the handle 22 is mounted, and a distal end 228 on which the ablation electrode 216 is disposed. Like the previously described probe shaft 14, the probe shaft 214 in this case is rigid or semi-rigid and comprises a tissue penetrating distal tip 230 to facilitate the percutaneous introduction of the ablation probe 210 into the patient. The probe shaft 214 has a metallic core and an insulation layer (both not shown) and may be sized in the same manner as the previous probe shaft 14.

The ablation probe 210 comprises a magnetic element 220 mounted on the probe shaft 214 just proximal to the distal tip 230 in the same manner as the previously described magnetic element 20. The ablation electrode 216 is formed on the probe shaft 214 proximal to the magnetic element 220 in the same manner as the previously described ablation electrode 18, e.g., by removing a portion of the insulation layer. The RF generator 12, and in particular, the positive terminal of the RF generator 12, is coupled to the electrical connector 36 carried by the handle 22 via an RF cable. The electrical connector 36 may be coupled to the ablation electrode 216 in the same manner that it was coupled to the ablation electrode 18 illustrated in FIG. 1, e.g., via discrete wires or the metallic shaft core. The RF generator 12, and in particular, the negative terminal of the RF generator 12, is coupled to an external dispersive electrode 218 via RF cable 225.

Figure 13:
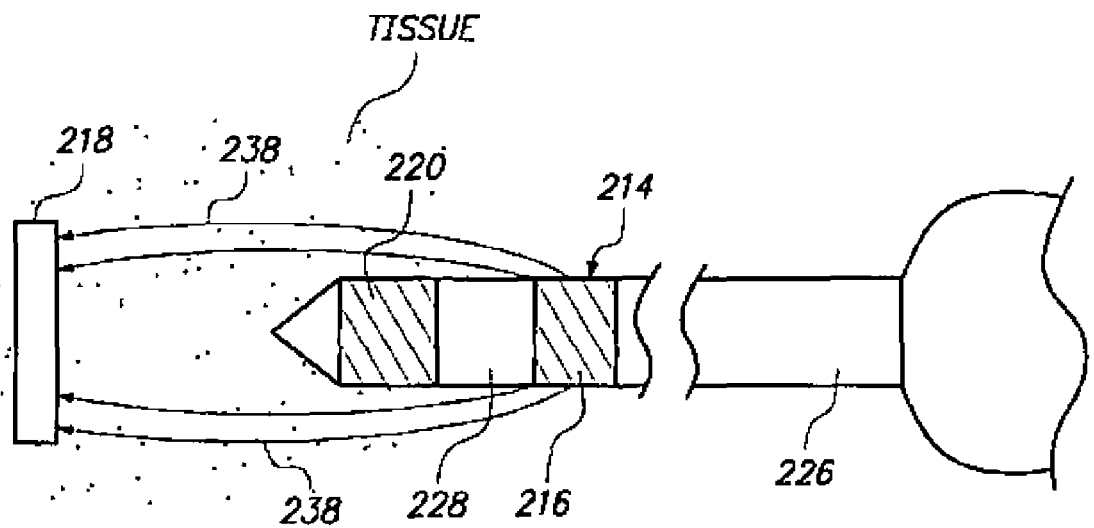
FIG. 13 is a partially cutaway plan view of the tissue ablation probe of FIG. 12, particularly illustrating the path that ablation energy is conveyed between bipolar electrodes of the tissue ablation probe.

As illustrated in FIG. 13, the RF current is delivered to the ablation electrode 216 in a monopolar fashion, which means that the ablation energy travels along a path 238, which originates at the ablation electrode 216 and terminates at the external electrode 218. In this arrangement, the ablation electrode 216 is configured to concentrate the energy flux in order to have an injurious effect on the surrounding tissue, and the external electrode 218, which is located remotely from the ablation electrode 216, has a sufficiently large area (typically 130 cm$^2$ for an adult), so that the current density is low and non-injurious to surrounding tissue. In the illustrated embodiment, the external electrode 218 may be attached externally to the patient, e.g., using a contact ground pad placed on the patient's flank.

Figure 14:
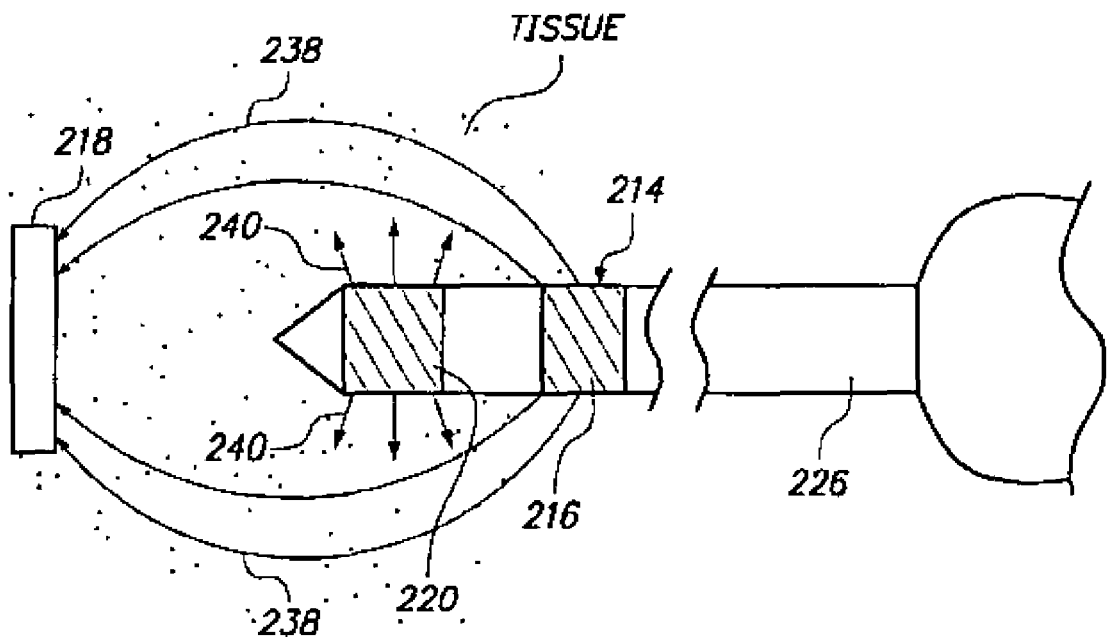
FIG. 14 is a partially cutaway plan view of the tissue ablation probe of FIG. 12, particularly illustrating the effect that the magnetic field generated by a magnetic element carried by the tissue ablation probe has on the ablation energy path.

As illustrated in FIG. 14, the magnetic element 220 generates a magnetic field that alters the path of the ablation energy conveyed through the tissue. In this embodiment, the magnetic field 240 generated by the probe shaft 214 urges the ablation energy 238 radially outward relative to the axis of the probe shaft 214. In particular, the magnetic flux lines 240 generated by the magnetic element 220 urges the ablation energy radially outward into the tissue relative to the probe axis. Thus, as with the previously described ablation probe 10, a greater volume of tissue is exposed to the ablation energy, thereby advantageously resulting in a larger lesion.

Figure 15A:
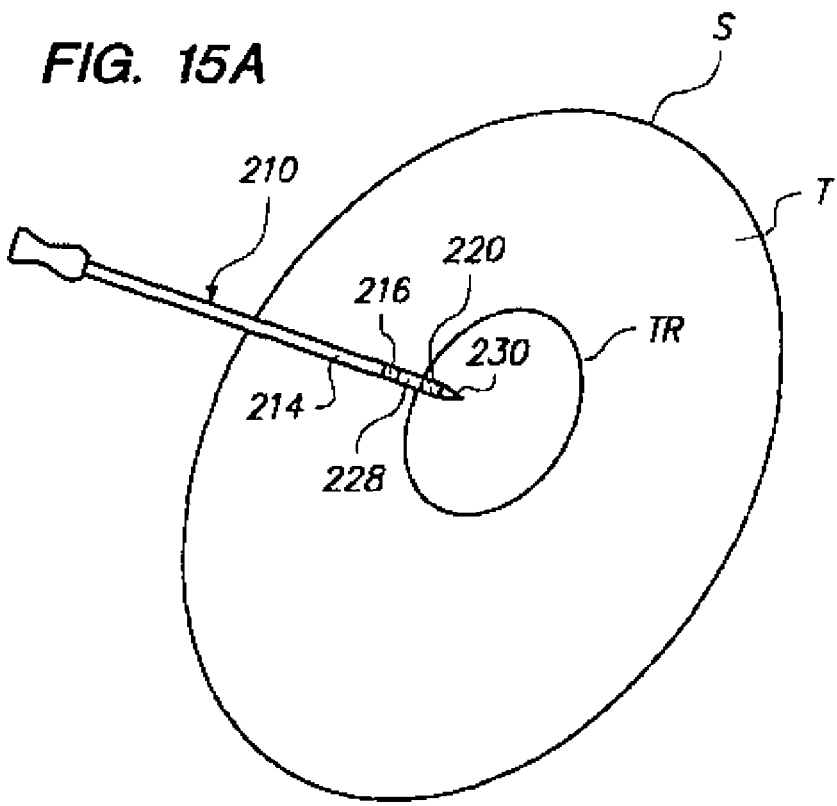
FIGS. 15A-15C are side views illustrating a method of ablating tissue using the tissue ablation probe of FIG. 12.
Figure 15B:
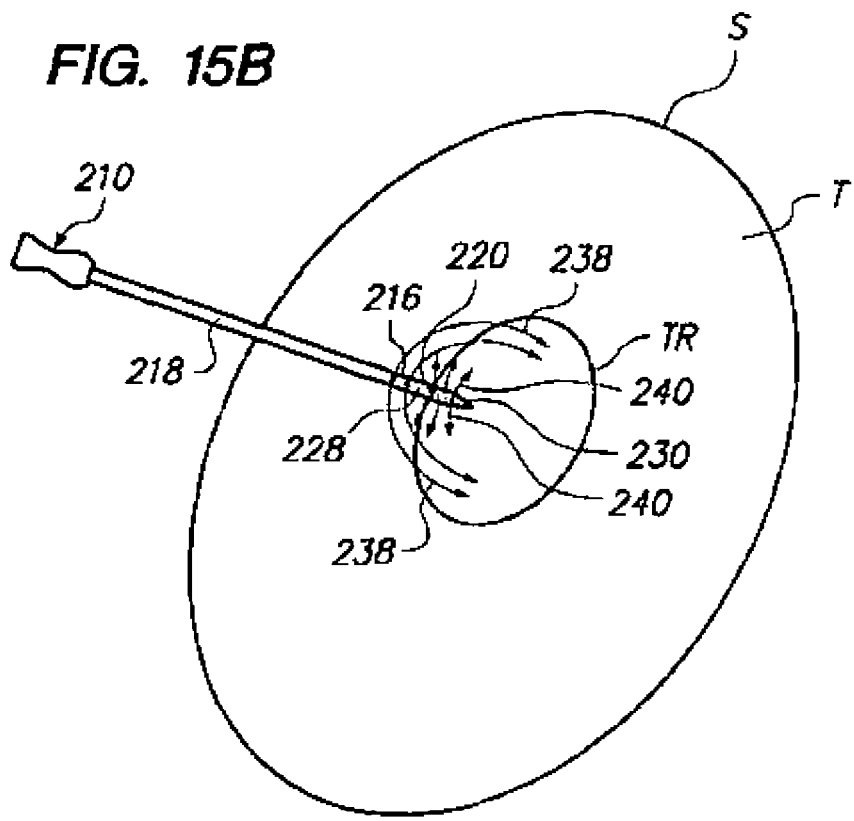
Figure 15C:
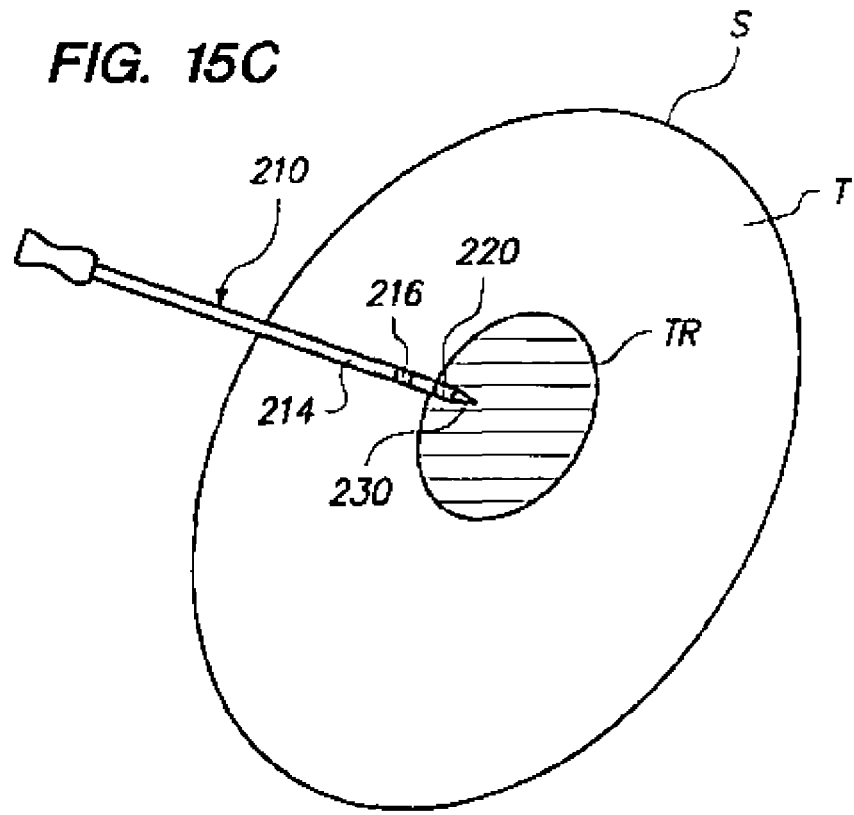

Referring to FIGS. 15A-15C, the operation of the tissue ablation probe 210 will now be described. The tissue ablation probe 210 is introduced through the tissue T in the same manner described above, with the exception that the ablation electrode 216 will be located at the proximal end of the treatment region TR (FIG. 15A). After the RF generator 12 (shown in FIG. 1) is connected to the electrical connector 36 and external electrode 218, and the external electrode 218 is properly attached to the skin of the patient, ablation energy is conveyed from the ablation electrode 216 to the external electrode 218 (FIG. 15B), while the probe shaft 214 generates the magnetic field 240 to urge the ablation energy 238 radially outward further into the treatment region TR. As a result, an ablation lesion L, which will eventually expand to include the entire treatment region TR, is created (FIG. 15C).

Figure 16:
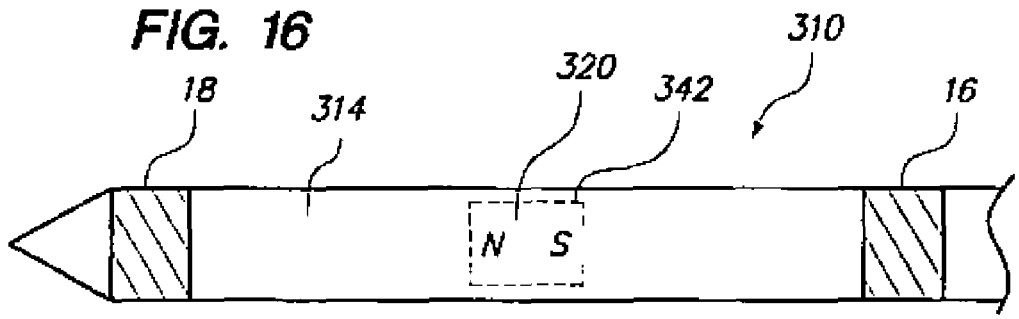
FIG. 16 is partially cutaway plan view of a tissue ablation probe constructed in accordance with still another embodiment of the present invention.

Although the previously described magnetic elements have been configured for radially urging ablation energy outward to create larger ablation lesions, tissue ablation probes with magnetic elements configured for augmenting the path of ablation energy other than in the radial direction can be used. For example, FIG. 16 illustrates a tissue ablation probe 310 that is similar to the tissue ablation probe 10 illustrated in FIG. 1, with the exception that the ablation energy conveyed by the ablation probe 310 is urged in a generally longitudinally direction.

In particular, the tissue ablation probe 310 comprises a probe shaft 314 that is identical to the previously described probe shaft 14, with the exception that it includes a cavity 342 located in the axial center of the shaft 314. The tissue ablation probe 310 further comprises a cylindrical bar magnet 320 suitably mounted within the cavity 342. In the illustrated embodiment, the bar magnet 320 has a North pole that points towards the distal ablation electrode 18 and a South pole that points towards the proximal ablation electrode 16.

Figure 17:
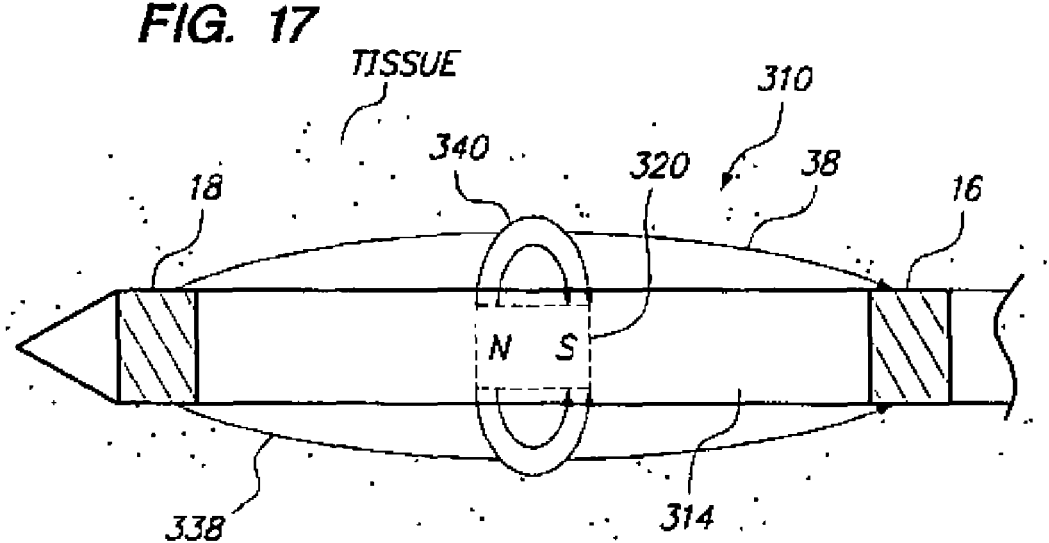
FIG. 17 is a partially cutaway plan view of the tissue ablation probe of FIG. 16, particularly illustrating the effect that the magnetic field generated by a magnetic element carried by the tissue ablation probe has on the path of ablation energy conveyed between bipolar electrodes of the tissue ablation probe.

Absent the magnetic element 320, the ablation energy will be conveyed between the proximal and distal ablation electrodes 16, 18 in the same manner illustrated in FIG. 4. However, the magnetic element 320 generates a magnetic field 340 that alters the path of the ablation energy 38 conveyed through the tissue. In this embodiment, the magnetic field generated by the magnetic element 320 urges the ablation energy 38 longitudinally along the axis of the probe shaft 314, as illustrated in FIG. 17. Through experimentation, it has been discovered ablation energy will be urged in the direction that the South pole of the magnetic element 320 points—in this case, in the proximal direction. Thus, it can be appreciated that an ablation lesion can be preferentially created in a particular direction. For example, if it is preferred that the ablation energy be urged in the distal direction, the magnetic element 320 can, instead, be mounted in the cavity 342 of the probe shaft 314, such that the South pole points in the distal direction.

Use of the tissue ablation probe 310 may be advantageous in situations where it is desired that the resulting ablation lesion be biased towards one of the ablation electrodes 16, 18. For example, referring to FIG. 18A-18C, the operation of the tissue ablation probe 310 in ablating a treatment region TR will now described. In this case, the treatment region TR is smaller than the span between ablation electrodes 16, 18, and thus, it is not desirable to create a lesion that would encompass both ablation electrodes 16, 18.

Figure 18A:
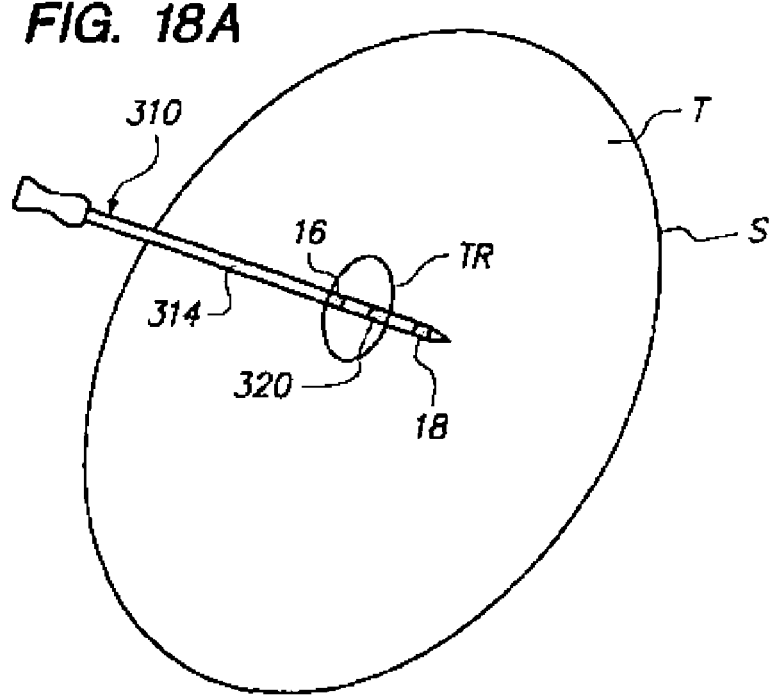
FIGS. 18A-18C are side views illustrating a method of ablating tissue using the tissue ablation probe of FIG. 16.
Figure 18B:
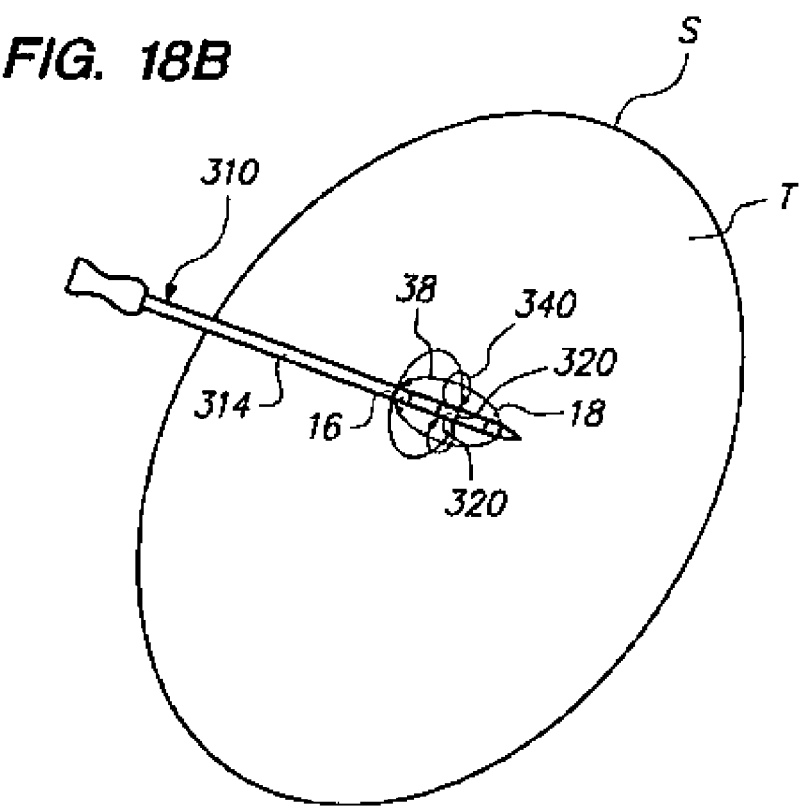
Figure 18C:
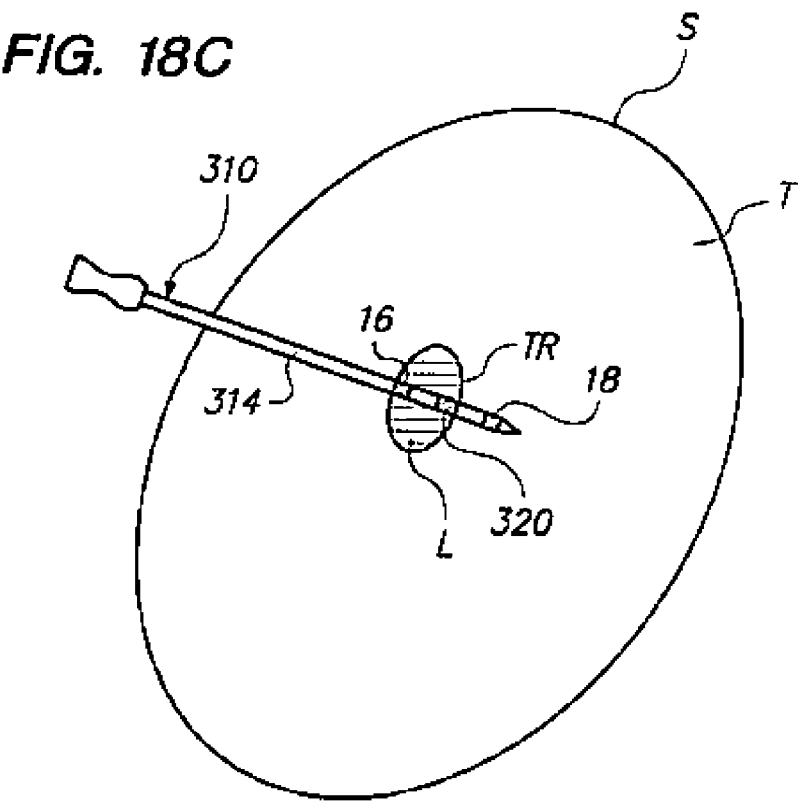

The tissue ablation probe 310 is introduced through the tissue T in the same manner described above with respect to FIG. 9A, with the exception that the distal ablation electrode 18 will be located distal to the treatment region TR, so that the proximal ablation electrode 18 is located in the proximal portion of the treatment region TR (FIG. 18A). After the RF generator 12 (shown in FIG. 1) is connected to the electrical connector 36, ablation energy 38 is conveyed between the ablation electrodes 16, 18, while the magnetic element 320 generates the magnetic field 340, which urges the ablation energy towards the proximal ablation electrode 16, and thus, the proximal end of the treatment region TR (FIG. 18B). As a result, an ablation lesion L, which will eventually expand to include the entire treatment region TR, is created (FIG. 18C). As illustrated, the ablation lesion L is not formed equidistantly between the ablation electrodes 16, 18, but rather is biased towards the proximal electrode 16.

Although the previously described tissue ablation probes take the form of monopolar and bipolar needle probes, magnetic elements can be incorporated into other types of ablation probes to alter their ablation energy paths. For example, monopolar and bipolar ablation probes with deployable needle electrode arrays, such as those described in U.S. Pat. No. 6,379,353, entitled "Apparatus and method for treating tissue with multiple electrodes"; U.S. Patent Publication 2002/0022864, entitled "Multipolar Electrode System for Radiofrequency Ablation"; U.S. patent application Ser. No. 09/663,048, entitled "Methods and Systems For Focused Bipolar Tissue Ablation," and U.S. patent application Ser. No. 11/030,229, entitled "Co-Access Bipolar Ablation Probe," all of which are hereby expressly incorporated herein by reference. In these cases, the magnetic element can either be incorporated into the cannula that houses the electrode arrays or on the inner slidable probe shaft that actuates deployment of the electrode arrays.

Magnetic elements can also be incorporated into co-access cannulae used to introduce monopolar and bipolar tissue ablation probes, along with other types of probes, such as biopsy probes, to alter the ablation paths created by the deployed electrode element(s). Such co-access cannulae are described in U.S. patent application Ser. Nos. 10/828,032 and 11/030,229, both of which are entitled "Co-Access Bipolar Ablation Probe", and both of which are hereby expressly incorporated herein by reference.

Magnetic elements can even be incorporated into devices other than the tissue ablation probes and any associated delivery cannulae, which devices can then be placed adjacent the electrode element(s) during the ablation procedure to advantageously alter that path of the ablation energy. In these cases, however, multiple entry points are generally required for introduction of the multiple devices into the patient, which may increase patient discomfort and recovery time.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A tissue ablation assembly, comprising:
an elongate probe device having an axis and an outer surface;
first and second electrode elements disposed on the outer surface of the probe device for conveying ablation energy therebetween; and
at least one magnetic element for substantially urging the ablation energy conveyed by the first and second electrode elements radially outward relative to the probe device axis, wherein the at least one magnetic element is axially located between the two electrode elements and is disposed on the outer surface of the probe device, and wherein there is no overlap between the at least one magnetic element and the first and second electrode elements.

2. The tissue ablation assembly of claim 1, wherein the elongate probe device is configured for being percutaneously introduced into tissue.

3. The tissue ablation assembly of claim 1, wherein each of the at least one magnetic element is a discrete magnet.

4. The tissue ablation assembly of claim 1, wherein the at least one magnetic element generates a magnetic field strength of at least 500 Oersteds.

5. The tissue ablation assembly of claim 1, wherein the at least one magnetic element generates a magnetic field strength of at least 5000 Oersteds.

6. The tissue ablation assembly of claim 1, further comprising a radio frequency (RF) generator operably coupled to the first and second electrode elements.

7. A tissue ablation assembly, comprising:
an elongate probe device having an axis;
at least one ablation electrode element carried by the probe device for conveying ablation energy; and
a ring magnet carried by the probe device, the ring magnet exhibiting at least four alternating magnetic poles circumferentially disposed around the probe device axis, the ring magnet comprising four arcuate magnetic sectors, wherein the four arcuate magnetic sectors are arranged circumferentially in a North-South, South-North, North-South, South-North arrangement.

8. The tissue ablation assembly of claim 7, wherein the elongate probe device is configured for being percutaneously introduced into tissue.

9. The tissue ablation assembly of claim 7, wherein the at least one electrode element comprises two electrode elements configured for conveying the ablation energy therebetween, wherein the ring magnet is axially located between the two electrode elements.

10. The tissue ablation assembly of claim 7, wherein the ring magnet generates a magnetic field strength of at least 500 Oersteds.

11. The tissue ablation assembly of claim 7, wherein the ring magnet generates a magnetic field strength of at least 5000 Oersteds.

12. The tissue ablation assembly of claim 7, wherein the at least four magnetic poles are equidistantly spaced around the probe device axis.

13. The tissue ablation assembly of claim 7, further comprising a radio frequency (RF) generator operably coupled to the at least one electrode element.

* * * * *